United States Patent [19]

Zaiger et al.

[11] Patent Number: Plant 7,065

[45] Date of Patent: Dec. 5, 1989

[54] PEACH TREE "ARTIC GEM"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 290,509

[22] Filed: Dec. 23, 1988

[51] Int. Cl.[4] ..... A01H 5/00

[52] U.S. Cl. ..... Plt./42

[58] Field of Search ..... Plt./42

*Primary Examiner*—Robert E. Bagwill

[57] ABSTRACT

The new and distinct variety of peach tree has the following unique combination of desirable features:

1. Vigorous upright growth.
2. Heavy and regular production.
3. Fruit with firm white flesh.
4. Fruit with a high degree of attractive red skin color.
5. Fruit with good flavor and eating quality.
6. Large fruit size, relatively uniform in size throughout the tree.

1 Drawing Sheet

ORIGIN OF THE VARIETY

Our new variety of peach tree was originated by us in the experimental orchard located at Modesto, Calif. as a second generation seedling from a cross between O'-Henry Peach (U.S. Plant Pat. No. 2,964) and Giant Babcock Peach (U.S. Plant Pat. No. 1,353). A selection having desirable characteristics, including firm white flesh, was made from the first generation and this selection was selfed to produce a large number of seedlings which were grown and maintained under close observation and the present variety which evidenced distinctive desirable characteristics was selected for asexual reproduction and commercialization.

ASEXUAL REPRODUCTION OF THE VARIETY

The present new variety of peach tree was asexually reproduced by budding, as performed at our experimental orchard located at Modesto, Calif., shows that the said characteristics described above come true to form and are established and transmitted through succeeding propagations.

SUMMARY OF THE VARIETY

The new and distinct variety of peach tree is of large size, vigorous, upright growth and a regular and productive bearer of large, firm, white flesh, freestone fruit with an attractive red skin color, good flavor and eating quality and the ability to ship to long distance markets; the fruit is further characterized in comparison to Giant Babcock Peach (U.S. Plant Pat. No. 1,353) by maturing 5 to 6 days later, having firmer white flesh with greater shipping and storage ability and a higher degree of attractive red skin color.

BRIEF DESCRIPTION OF THE PHOTOGRAPHS

The accompanying photographic illustrations show typical specimens of the fruit and foliage of the new variety, an exterior and sectional view of the fruit being shown with a stone remaining in place and the upper and lower surface of the leaves being illustrated. These photographs were taken shortly after being picked at maturity (firm ripe) and the colors are as nearly true as is reasonably possible in a color representation of this type.

DESCRIPTION OF THE VARIETY

The botanical details of this new and distinct variety of peach tree, its fruit and foliage are based upon observations of specimens grown at Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Productivity.*—Productive.
- *Bearer.*—Regular.
- *Growth.*—Upright.
- *Density.*—Medium Dense.

Trunk:
- *Size.*—Medium to stocky.
- *Texture.*—Medium shaggy.
- *Color.*—Brown.

Branches:
- *Size.*—Medium.
- *Texture.*—Smooth to medium rough.
- *Lenticels.*—Medium size. Medium number.
- *Color.*—Brown to grayish brown.

Leaves:
- *Size.*—Large. Average length — 7⅛". Average width — 1⅜".
- *Form.*—Lanceolate. Acutely pointed.
- *Thickness.*—Medium.
- *Margin.*—Crenate.
- *Petiole.*—Average length — 9/16". Average width — 3/32".
- *Glands.*—Range 2 to 6. Average number 4. Reniform. Positioned on upper portion of petiole and lower portion of leaf blade.
- *Color.*—Upper surface — dark green (27-F-6) to (27-F-8). Lower surface — grayish green (28-E-6) to (27-E-8).

Flower buds:
- *Size.*—Large.
- *Form.*—Plump.
- *Pubescence.*—Pubescent.

Flowers:
- *Size.*—Large — showy.

*Blooming period.*—First bloom — Mar. 1, 1985. Full bloom — Mar. 5, 1985. Varies slightly due to weather variations.

*Pollen.*—Present.

*Color.*—Pink.

Fruit:

*Maturity when described.*—Firm ripe.

*Date of first picking.*—July 19, 1985.

*Date of last picking.*—July 25, 1985.

*Size.*—Large. Average diameter axially 2¾" to 2 15/16". Average transversely in suture plane 3" to 3¼".

*Form.*—Globose, retuse at stem end. Some fruit slightly larger on one side of suture.

*Suture.*—Shallow.

*Ventral surface.*—Usually round, some fruit lipped on one side.

*Apex.*—Rounded to slight retuse.

*Base.*—Retuse.

*Cavity.*—Rounded to slightly elongated in suture plane. Average depth — ½". Average width — 11/16".

Skin:

*Thickness.*—Medium.

*Texture.*—Medium. Tenacious to flesh when firm ripe. Free when soft ripe.

*Tendency to crack.*—None.

*Down.*—Moderate. Medium length.

*Color.*—Ground color — yellowish white (3-A-2) to light yellow (3-A-4). Overspread with red — (9-B-8) to lake red (9-C-8).

Flesh:

*Texture.*—Firm.

*Fibers.*—Few — tender.

*Amygdalin.*—Undetected.

*Ripens.*—Evenly.

*Flavor.*—Mild.

*Juice.*—Moderate.

*Aroma.*—Moderate.

*Eating quality.*—Very Good.

*Color.*—Oyster white to yellowish white (2-A-2) to (3-A-2). Pit cavity — red to crayfish red (8-C-8) to (9-B-8).

Stone:

*Type.*—Freestone.

*Size.*—Large. Average length — 1⅜". Average width — 1". Average thickness — 9/16".

*Form.*—Ovid.

*Base.*—Straight to slightly oblique.

*Sides.*—Equal to unequal.

*Surface.*—Furrowed toward apex, pitted toward base.

*Ridges.*—Round.

*Tendency to split.*—Very slight.

*Color.*—Brown to reddish brown (8-C-4) to (8-D-5).

Use: Dessert.

*Market.*—Local and long distance.

Keeping quality: Good.

Shipping quality: Good.

The present new variety of peach tree and its fruit herein described may vary in slight detail due to climatic, soil type and cultural practices under which the variety may be grown; the present description being that of the variety grown under the ecological conditions prevailing at Modesto, Calif.

The following is claimed:

1. A new and distinct variety of peach tree substantially as illustrated and described, which is of large size, vigorous, upright growth and a regular and productive bearer of large, firm, white flesh, freestone fruit with good flavor and eating quality; the fruit is further characterized in comparison to Giant Babcock Peach (U.S. Plant Pat. No. 1,353) as having firmer white flesh and greater shipping and storage quality, a higher degree of attractive red skin color and maturing 5 to 6 days later.

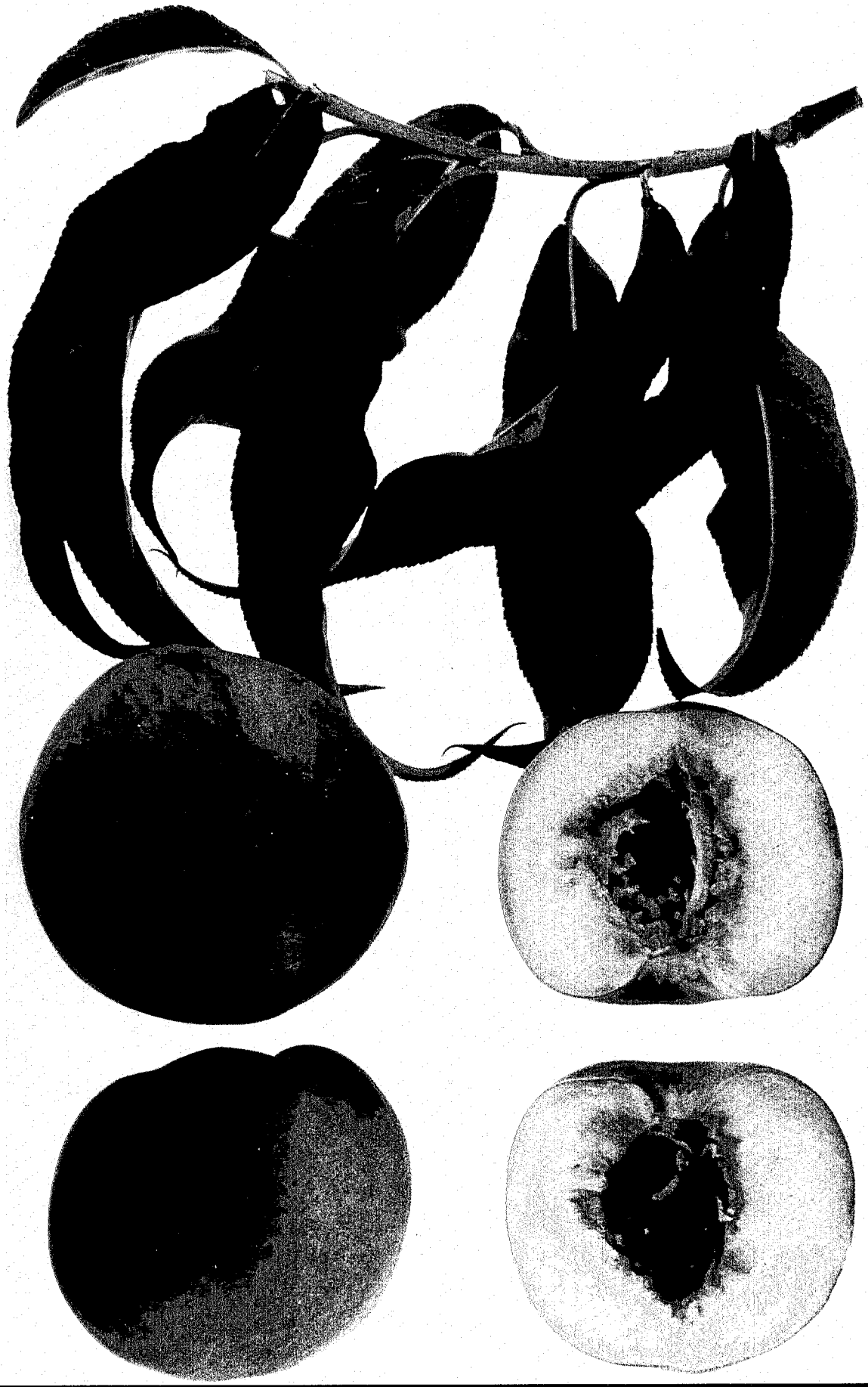

* * * * *